(12) United States Patent
Satoshi

(10) Patent No.: US 7,899,218 B2
(45) Date of Patent: Mar. 1, 2011

(54) GENDER IDENTIFICATION METHOD

(75) Inventor: Nishino Satoshi, Saitama (JP)

(73) Assignee: Nihondensikougaku Co., Ltd., Tochigi (JP)

( * ) Notice: Subject to any disclaimer, the term of this patent is extended or adjusted under 35 U.S.C. 154(b) by 903 days.

(21) Appl. No.: 10/586,057

(22) PCT Filed: Jan. 20, 2005

(86) PCT No.: PCT/JP2005/001035
§ 371 (c)(1),
(2), (4) Date: Jul. 9, 2007

(87) PCT Pub. No.: WO2005/070301
PCT Pub. Date: Aug. 4, 2005

(65) Prior Publication Data
US 2007/0274572 A1    Nov. 29, 2007

(30) Foreign Application Priority Data
Jan. 22, 2004 (JP) .............................. 2004-045440

(51) Int. Cl.
*G06K 9/00* (2006.01)
(52) U.S. Cl. ................. 382/118; 382/100; 382/115; 382/325
(58) Field of Classification Search .............. 382/100, 382/115, 118, 325
See application file for complete search history.

(56) References Cited

U.S. PATENT DOCUMENTS 5,163,094 A * 11/1992 Prokoski et al. ............. 382/118
6,173,068 B1 * 1/2001 Prokoski ..................... 382/115

FOREIGN PATENT DOCUMENTS

| JP | 8-249444 | 9/1996 |
| JP | 10-293837 | 11/1998 |

(Continued)

OTHER PUBLICATIONS

Jingu Heo, "Fusion of Visual and Thermal Face Recognition Techniques: A Comparative Study" University of Tennessee, Knoxville, Oct. 2003, available at http://imaging.utk.edu/publications/papers/dissert.*

(Continued)

*Primary Examiner*—Jingge Wu
*Assistant Examiner*—Stephen R Koziol
(74) *Attorney, Agent, or Firm*—Connolly Bove Lodge & Hutz LLP

(57) ABSTRACT

Infrared face image data is obtained (11) on a person (P) who is a subject of discrimination using an image signal (VDA) from a television camera (2A); the cheek region and jaw region temperatures of the subject (P) are sampled based on the infrared face image data; the averages of the temperatures are calculated (15, 16); cheek data/jaw data is calculated (17); and a cheek emphasized variance value is calculated (18). The cheek data/jaw data and cheek emphasized variance value are mapped on an XY plane (19), and gender discrimination of the person (P) is conducted based on the result. In addition, gender discrimination is conducted using the cheek data/jaw data (21) and gender discrimination is conducted using the cheek emphasized variance value (22), and gender identification is conducted in accordance with agreement between two or more of the multiple gender discrimination results (24).

1 Claim, 11 Drawing Sheets

FOREIGN PATENT DOCUMENTS

JP          2001-216515          8/2001

OTHER PUBLICATIONS

Satoshi Nishino et al., "Gender Determining Method using Thermography" 2004 International conference on Image Processing (ICIP) Oct. 2004, pp. 2961-2965.*

Prokoski et al. "Infrared Identification of Faces and Body Parts" Springer Biometrics: Personal Identification in Networked Society, pp. 191-212, 2002.*

Gutta et al. "Mixture of experts for classification of gender, ethnic origin, and pose of human faces," IEEE Transactions on Neural Networks, vol. 11 Issue 4, pp. 948-960, Jul. 2000.*

Nishino et al., "Man and Woman Distinction Using Thermography", The Institute of Electroics, Information and Communication Engineers, System 2, Mar. 8, 2004, p. 181.

Yamamoto et al., "Influence of Room Temperature on Skin Temperature, Tympanic Temperature and Thermal Sensation by Bed Bathing of the Back", Japanese Journal of Physiological Anthropology, vol. 8, No. 4, Nov. 2003, pp. 217-223.

Okamoto et al., "Comparison of Temperature Rhythms in Male and Female Human—Using the Visual Inspection and Consiner Method", Dept. of Psychiatry and Neurogy, Hamamatsu University School of Medicine, vol. 33, No. 7, Jul. 1, 1991, pp. 485-488.

Iriki et al., "Oral Temperature of Healthy Japanese—the points at Issue in Thermometry and the Compairson With Axillary Temperature", vol. 62, No. 1 Jul. 1, 1988, pp. 165-165.

Yoshiue et al., "Seijochi Ijochi Taion", Sogo Rinsho, vol. 34, Aug. 10, 1985, pp. 1599-1606.

Kihara et al., "Seijo Seijin Sokkonbu Hifuon no Shinkei Seirigakuteki Kento-Seisa, Sayusa, Oyobi Kareiteki Henka ni Tsuite", Japanese Journal of Geriatrics, vol. 21, No. 4, pp. 381-382, 1984.

International Search Report No. PCT/JP2005/001035, dated Feb. 10, 2005, 2 pgs.

* cited by examiner

CHEEK TEMPLATE

JAW TEMPLATE

GENDER IDENTIFICATION METHOD

This application is a National Phase application of PCT/JP2005/001035, filed Jan. 20, 2005, which claims priority to JP 2004-045440, filed Jan. 22, 2004.

TECHNICAL FIELD

The present invention relates to a method for distinguishing between human males and females.

BACKGROUND ART

Methods for distinguishing between human males and females have been proposed in various fields. For example, Unexamined Japanese Patent Application JP-A-2001-218020 teaches an image processing method that identifies the gender of a person seen in a camera photo based on the person's appearance and carries out image data processing for enhancing the looks of the photographed subject based on the result of the gender identification. Unexamined Japanese Patent Application 10-293837 teaches a system for acquiring marketing information by installing a gender identification system at the entrances of various kinds of halls, stores and the like and counting the number males and females among the visitors.

Conventional gender identification methods distinguish the gender of a person by photographing the person with a television camera or digital camera, extracting from those portions of the acquired data related to the person certain portions of interest, such as the face, hands, shoes and personal effects, and analyzing the nature thereof. The specific judgment criteria include, for instance, the center of gravity of the hair mass, how long the arms are kept folded, size of handbag, how long a hand is kept in a pocket, facial makeup, and whether or not the subject is wearing lipstick.

The conventional gender identification methods are thus based on characteristics of the human subject that a person can change intentionally, such appearance and mannerisms, and are therefore apt to be unreliable. Although methods for identifying gender based on voice information are also known, the discrimination is unreliable in this case, too, owing to use of, for example, a technique employing tone of voice; and, moreover, these methods have a drawback in that the scope of use is severely limited by the fact that in order to be able to use voice information the subject must be made to say something.

An object of the present invention is to provide a gender identification method that overcomes the aforesaid shortcomings of the prior art.

Another object of the present invention is to provide a gender identification method that utilizes a bio-characteristic inherent to the human body.

DISCLOSURE OF THE INVENTION

This invention utilizes a bio-characteristic that a human cannot modify at will. Specifically, it utilizes the fact that differences exist between human males and females in the temperature and temperature distribution of the hands and face.

This invention was accomplished on the basis of knowledge obtained through a study of differences between males and females in the temperature and temperature distribution of the hands and face, namely the findings that the body temperature tends to be high in males and low in females because, medically speaking, basal metabolism is high in males and low in females, that females generally have a higher percentage of body fat and more fat at the body surface than men because they secrete the female hormone estrogen, and that females tend to have a lower body surface temperature than men because radiation of body heat is blocked owing to the fact that fat has lower thermal conductivity than muscle. This characteristic is observed at exposed regions not covered with clothing, which makes it advantageous to perform gender identification using the temperature and temperature distribution at the face and hands.

The inventor first quantitatively investigated the influence of ambient temperature on facial temperature. Specifically, three men and three women of the same age were selected as test subjects. In a room of constant ambient temperature, the cheeks and jaws of the subjects were imparted with temperature changes using warming pads and cooling pads, and data was gathered regarding the time-course change in facial temperature. Specifically, warming pads were first kept in contact with each subject's cheek and jaw for a certain time period (5 minutes), whereafter the warming pads were removed and the time-course change in the cheek and jaw temperatures was measured. The first temperature measurement was made when 5 seconds had passed and measurements were then made every 15 seconds until 125 seconds had passed. Similar measurements were then made using cooling pads instead of warming pads.

Upon completion of the measurements, a cheek temperature sampling template and a jaw temperature sampling template, both shown in FIG. 1, were used to measure the average cheek temperature and average jaw temperature at the sampling regions of each subject. The value obtained by dividing the average cheek temperature by the average jaw temperature (hereinafter called "cheek/jaw"), for the sampling region of each subject, was scaled on the vertical axis (the cheek data/jaw data being scaled on the horizontal axis is scaled for time in FIG. 2), so that FIG. 2 shows how this value changed with respect to temperature change, i.e., passage of time. The jaw and cheek were exposed to the same ambient temperature and consequently exhibited similar temperature change. The influence of the ambient temperature could therefore be eliminated by focusing on the cheek data/jaw data. The fact that the ratio stayed substantially constant over passage of time following warming with the warming pads, i.e., even though the ambient temperature changed, means that FIG. 2 shows that the ratio was not affected by the ambient temperature.

So, in the final analysis, FIG. 2 shows values of the cheek temperature normalized by the jaw temperatures.

The following conclusions can be drawn from the results shown in FIG. 2:

1. The value of cheek data/jaw data was substantially constant for both males and females irrespective change in ambient temperature 2. "Cheek/jaw" tended to be large for men (around 1.2-1.5, i.e., cheek temperature was high) and small for women (around 1.0-1.2, i.e., cheek temperature was low).

In other words, this value is a characteristic enabling differentiation of males and females without influence from ambient temperature change because it is unaffected by change in the ambient temperature and differs between men and women.

Next, the subject cheek temperature was sampled using the cheek region temperature template shown in FIG. 3 and how the temperature of the sampled region was affected by the ambient temperature was studied. Two males and two females selected as subjects were kept in a room of 24° C. ambient temperature for about 10 minutes, whereafter the cheek temperatures of the subjects was sampled using the templates as the air-conditioned temperature was raised to 27° C. in increments of one degree. Of the so-sample data, that for one male is shown in FIG. 4.

It can be seen from FIG. 4 that as the ambient temperature increased, the histogram as a whole shifted in the direction of higher Level (temperature) with substantially no change in shape and area (approximately equal to variance). The same tendency was found for the other male. The females exhibited a similar tendency in a smaller Level region than the males. It can therefore be concluded that the male and female characteristics were maintained, with the variance being unaffected by ambient temperature. From this it follows that the variance at the cheek region is effective as a characteristic value for discriminating gender without influence from ambient temperature.

FIG. 5 shows an example of the cheek temperature distribution (approximately equal to variance) of a male and a female. It can be seen from FIG. 5 that average cheek temperature was higher for the male and that the temperature (Level) distribution was narrower in range in the case of the male, and in the case of the female the distribution range was lower in temperature and broader than that of the male. From FIG. 5 it can be considered that the difference in variance value between males and females arises because females have fat spread broadly centered on the cheek.

The difference in the data between males and females as regards variance value can be effectively accentuated by applying a special technique to the data processing. Equation (1) below represents average value, Equation (2) represents variance value and Equation (3) represents emphasized variance value.

$$\overline{X} = \frac{1}{n}\sum_{i=1}^{n} X_i \quad (1)$$

$$V = \frac{1}{n}\sum_{i=1}^{n} (X_i - \overline{X})^2 \quad (2)$$

$$E = \frac{1}{n}\sum_{i=1}^{n} (X_i - \overline{X})^4 \quad (3)$$

Equation (3) used here to accentuate the difference is obtained by changing the second power notation of Equation (2) according to the general definition to the fourth power notation.

In the foregoing equations, n is the pixel number of the sampled region and $X_i$ is the Level of the individual pixels of the sampled region. In this specification, the value obtained from Equation (3) is called the "emphasized variance value." It is obvious from a comparison of FIGS. 5, 6 and 7 that this emphasized variance value facilitates discrimination between males and females by expanding the male-female separation. FIG. 5 represents the original histogram, while FIGS. 6 and 7 represent the $X_i$–$\overline{X}$ second power and fourth power terms of the variance and emphasized variance values corresponding to $X_i$. By comparing FIGS. 6 and 7 it can be seen that the male-female separation is clearly larger in the case of the emphasized variance value of FIG. 7 than in the case of the variance value of FIG. 6.

In addition to the difference in temperature between males and females discussed above, there is also a difference in temperature distribution. It can be seen from FIG. 5 that the temperature distribution range is narrow for males and broad for females. This is because male fat is concentrated in a small area, while in females it is distributed over a broad area. Since the state of distribution is a bio-characteristic, it is not easily affected by ambient temperature. Gender identification can therefore be conducted based on difference in the distribution state by, for example, using the aforesaid emphasized variance value. The present invention is thus founded on a medical principle and utilizes a bio-characteristic that a person cannot modify at will and, as such, provides a gender identification method superior to the prior art methods.

When only the emphasized variance value of the cheek temperature is used, misidentification may occur for some reason. It is therefore preferable for boosting reliability to further incorporate two among 1 to 5 below to create a three-way combination, carry out a statistical discrimination (using Mahalanobis distance, for example) with respect thereto, and when two of the results are the same, adopting that result as the discrimination result:

1. Cheek emphasized variance value,
2. [Cheek/jaw]: Value obtained by dividing average cheek temperature by average jaw temperature,
3. Average cheek temperature,
4. Average jaw temperature,
5. Hand emphasized variance value.

BEST MODE OF CARRYING OUT THE INVENTION

In order to set out the present invention in more detail, an explanation will be made with reference to the attached drawings.

Figure 1:
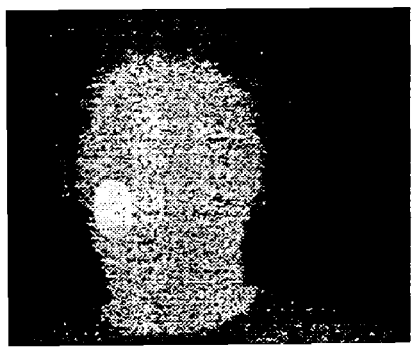
FIG. 1 is a set of photographs showing a jaw temperature sampling template and a cheek temperature sampling template.
Figure 1:
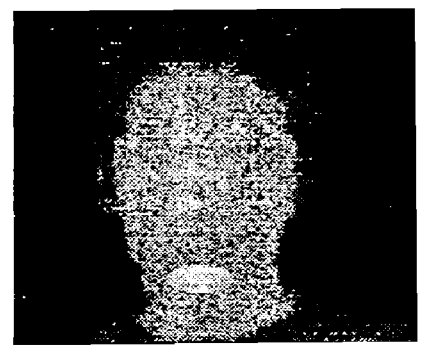
Figure 2:
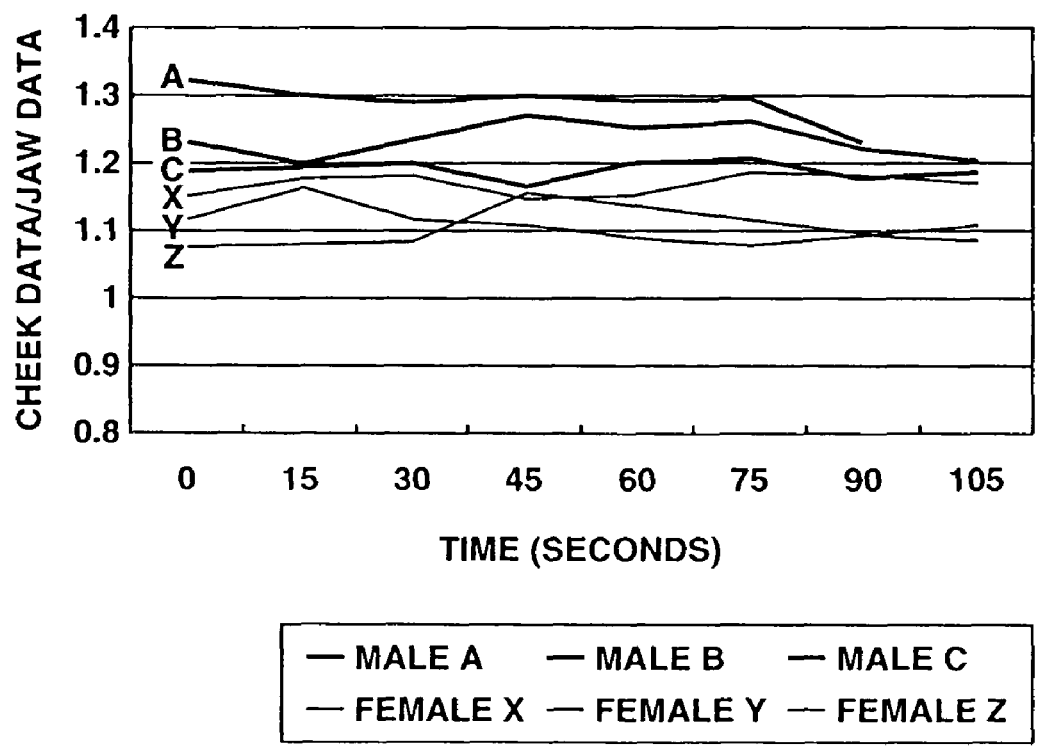
FIG. 2 is a graph showing the influence of ambient temperature to a normalized value obtained by dividing the average temperature in a cheek temperature sampling template by the average temperature in a jaw temperature sampling template. In other word, [Cheek/jaw] shows almost no influence by ambient temperature in FIG. 2.
Figure 3:
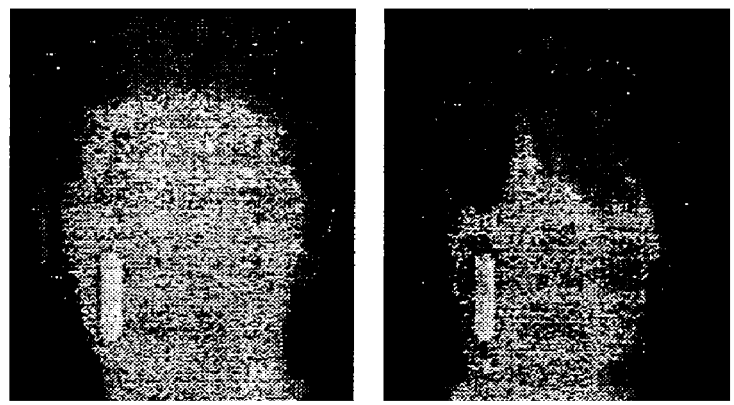
FIG. 3 is a set of photographs showing cheek temperature sampling templates for obtaining emphasized variance values.
Figure 4:
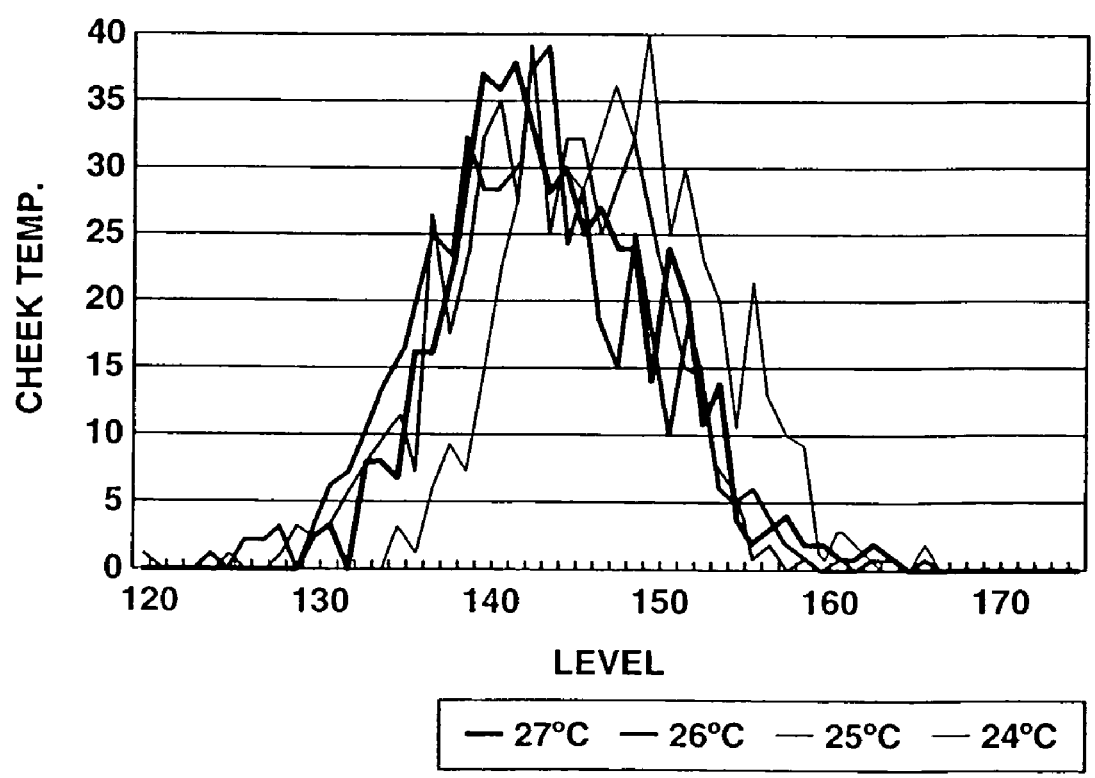
FIG. 4 is a graph showing influence of ambient temperature on the temperature distribution in a cheek temperature sampling template for obtaining emphasized variance value of a male.
Figure 5:
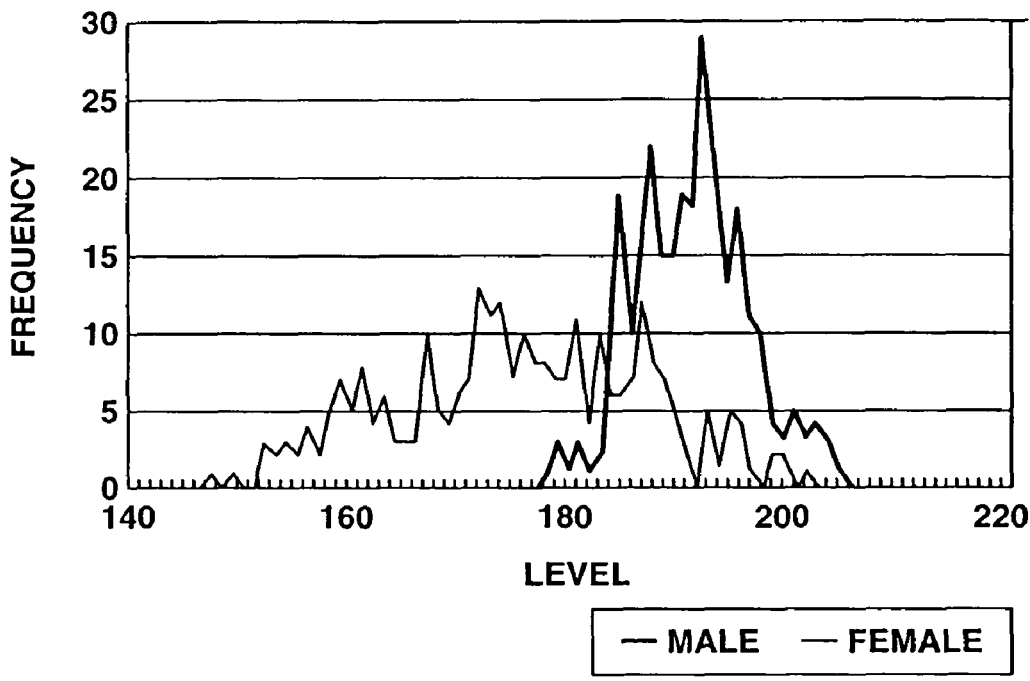
FIG. 5 shows histograms of temperature in cheek temperature sampling templates of a male and a female.
Figure 6:
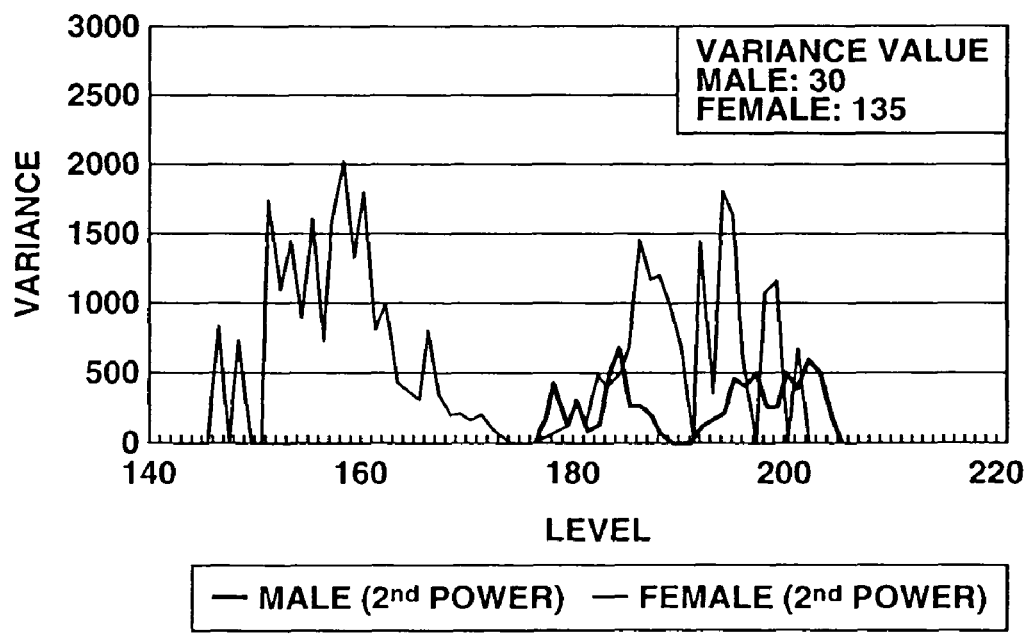
FIG. 6 is a graph showing difference in distribution between a male and a female.
Figure 7:
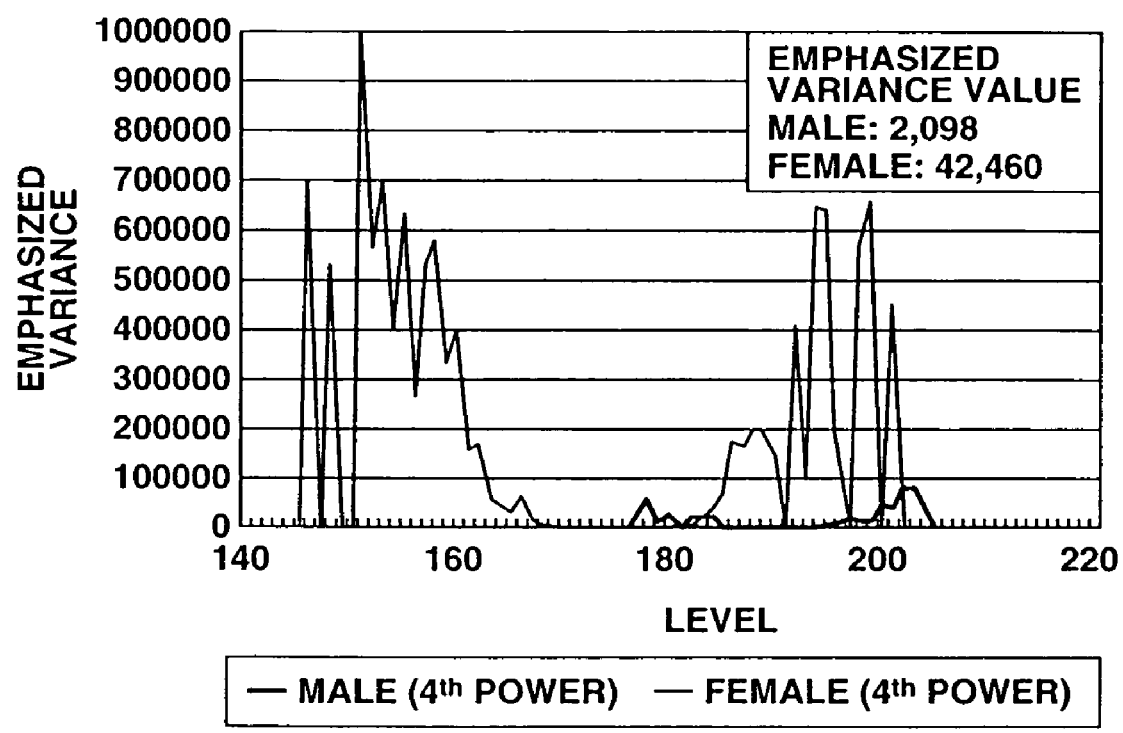
FIG. 7 is a graph showing difference in cheek emphasized variance value between a male and a female.
Figure 8:
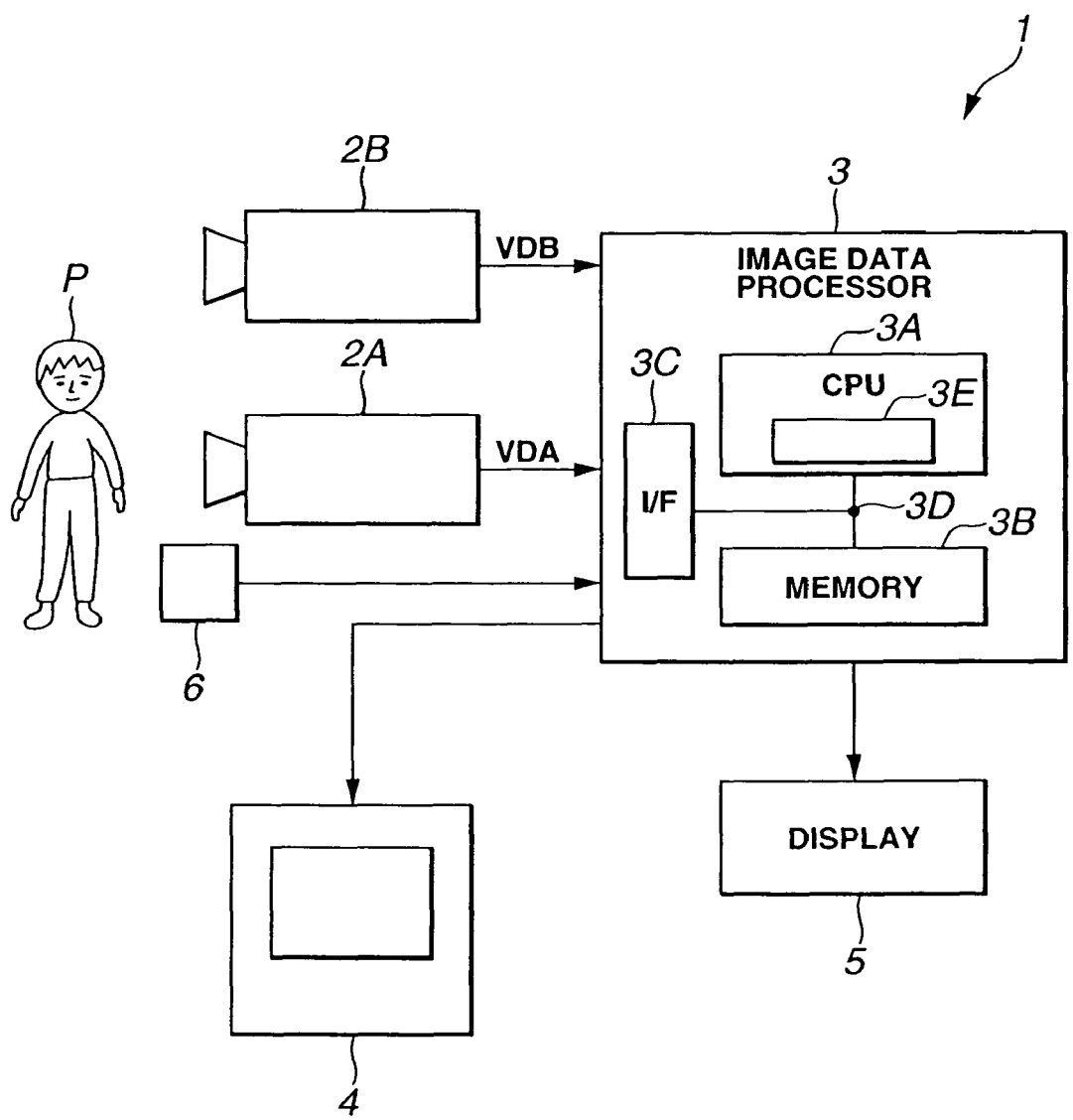
FIG. 8 is a block diagram showing an embodiment of the present invention.

FIG. 8 shows an embodiment of the gender identification method according to the present invention. The gender identification system 1 shown in FIG. 8 is installed at the entrance of a building not shown in the drawing and is configured to discriminate whether each person P about to enter the building is a male or a female and show the entering person P a display in accordance with the discrimination result. The gender identification system 1 is equipped with a television camera 2A for taking infrared images that is installed at the entrance to enable photographing of at least the faces of persons P about to enter the building. An image signal VDA from the television camera 2A is sent to an image data processor 3, where it is subjected to processing for discriminating between males and females as explained later, and is sent to a monitor unit 4 so that the situation at the entrance can be grasped through the monitor unit 4 at remote location (security room), for example. Although a configuration is adopted here that sends the image signal VDA to the monitor unit 4 via the image data processor 3, a configuration that sends the image signal VDA directly to the monitor unit 4 can be adopted instead. The symbol 5 designates a display comprising a liquid crystal display device for presenting a display to the person P. Symbol 6 designates a pushbutton switch that a person P desiring to enter is required to operate.

The image data processor 3 is constituted as a micro computer system of a conventional configuration comprising a central processing unit (CPU) 3A, a memory 3B and an input/output interface (I/F) 3C, which are interconnected by a bus 3D. An image data processing program having gender discrimination capability explained later is stored in a memory 3E of the central processing unit (CPU) 3A and the image signal VDA from the television camera 2A is processed in accordance with this image data processing program.

Figure 9A:
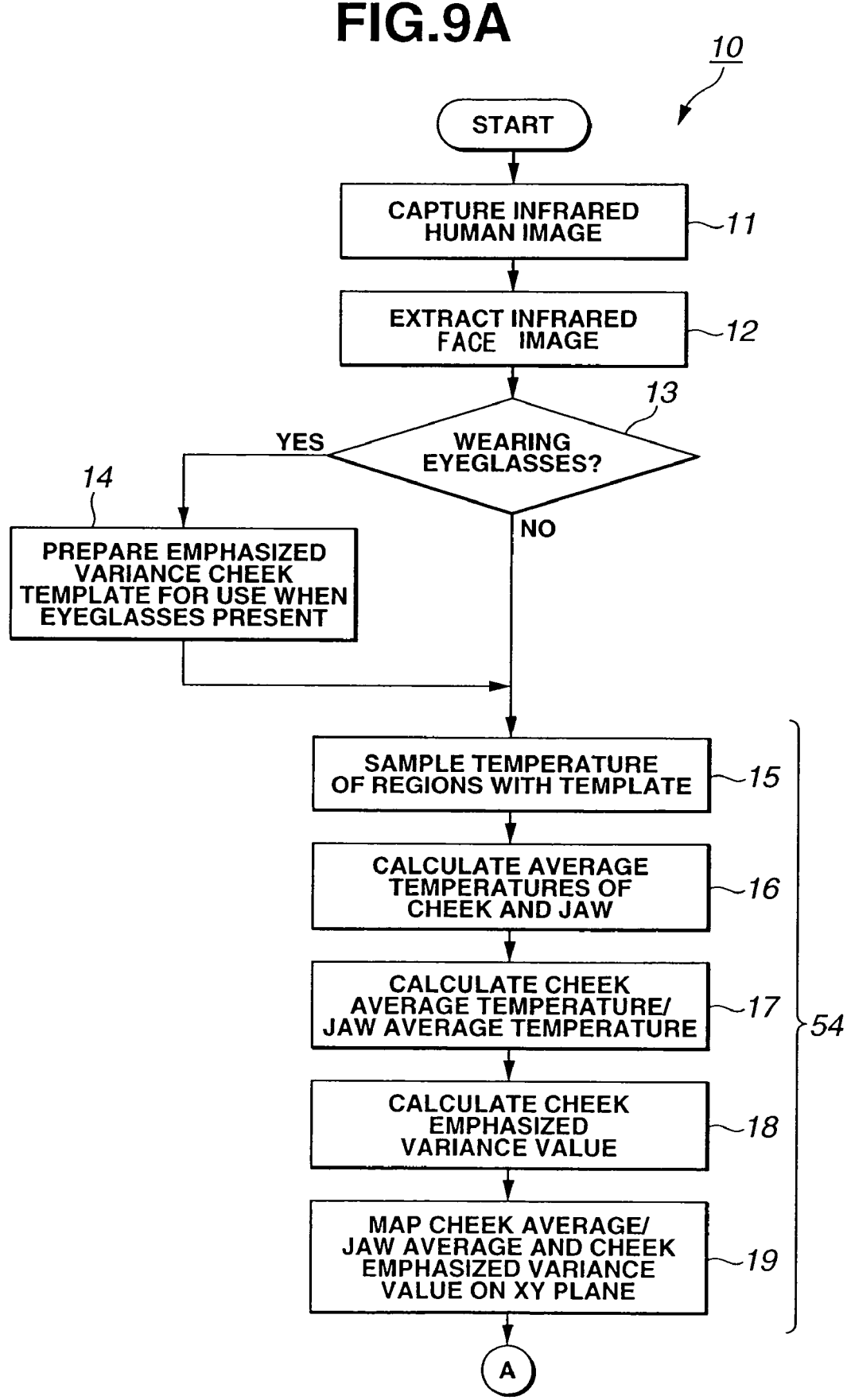
FIG. 9A is a partial flowchart of an image data processing program executed in an image data processor of FIG. 8.
Figure 9B:
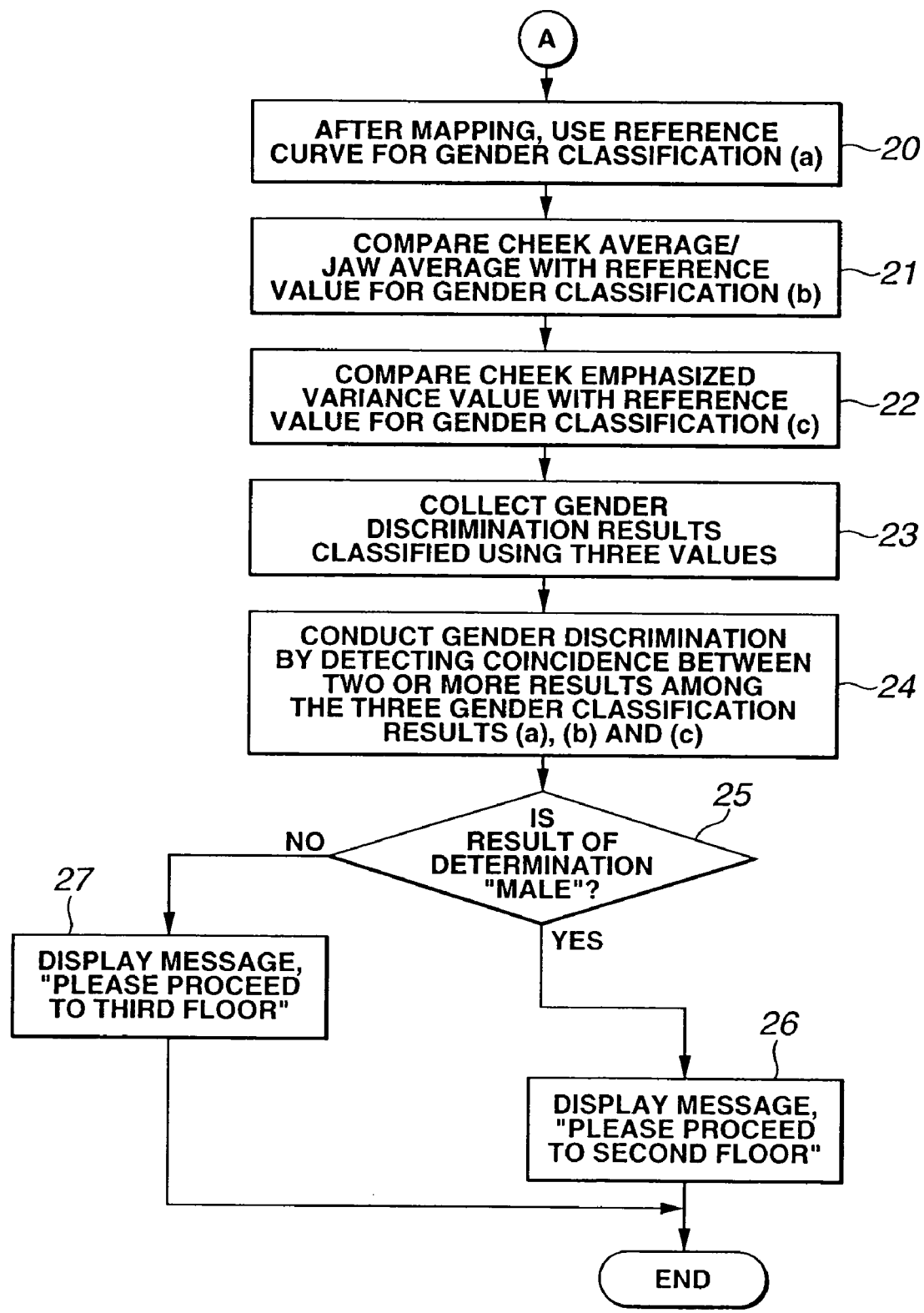
FIG. 9B is a partial flowchart of an image data processing program executed in the image data processor of FIG. 8.

FIGS. 9A and 9B are a flowchart showing the image data processing program stored in the memory 3E. The image data processing program 10 is executed every time the pushbutton switch 6 is pushed. Once execution of the image data processing program 10 has commenced, infrared human image capture processing for fetjawg the image signal VDA is conducted in Step 11. Then, in Step 12, infrared face image extraction processing is conducted for extracting a face image of the person P from the data captured in Step 11.

Figure 10:
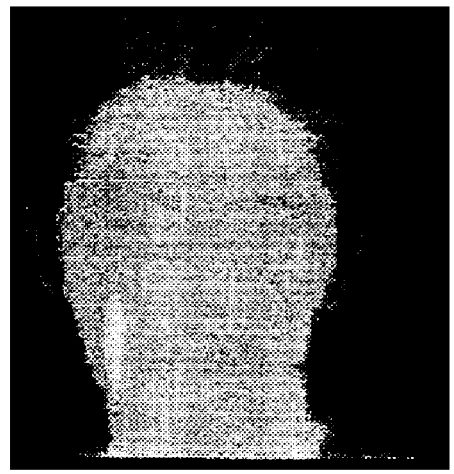
FIG. 10 is a photograph showing a cheek temperature sampling template that eliminates the influence of eyeglasses.
Figure 15:
FIG. 15 is a photograph showing a hand temperature sampling template.

In the following Step 13, it is checked based on the infrared face image extracted in Step 12 whether the person P is wearing eyeglasses. When the person P is wearing eyeglasses, the discrimination result in Step 13 becomes YES and control passes to Step 14, in which a cheek emphasized variance value template for use when eyeglasses are present, shown in FIG. 10, obtained by slightly removing the upper portion of the ordinary template is prepared, and then to Step 15. When it is found in Step 13 that eyeglasses are not present, the result in Step 13 becomes NO and control passes to Step 15. An ordinary template used in cases other than when eyeglasses are present is already available in Step 15. And in Step 15, one of the templates is selected according to whether or not eyeglasses are present and the temperatures of the cheek and jaw regions of the person P are sampled.

In Step 16, the averages of the temperatures of the cheek and cheek regions sampled in Step 15 are calculated, and next, in Step 17, the ratio of the cheek average temperature to the jaw average temperature (cheek average temperature/jaw average temperature) is calculated. In Step 18, the emphasized variance value of the cheek region temperature sampled in Step 15 is calculated in accordance with Equation (3). In Step 19, processing is conducted for two-dimensionally mapping the values calculated in Steps 17 and 18.

Next, in S20, a discrimination method utilizing a Mahalanobis distance determined beforehand is applied for gender determination using a curve for classification into two categories (i.e., male and female), thereby obtaining classification result (a). In Step 21, the cheek average temperature/jaw average temperature is compared with a gender classification reference value for gender determination, thereby obtaining classification result (b). In Step 22, the cheek emphasized variance value calculated in Step 18 is compared with a gender classification reference value determined beforehand, thereby carrying out gender classification (c).

The three gender classification results that were obtained with respect to the input infrared face image of the person P who is the subject of the discrimination and were classified as (a), (b) and (c) are collected in Step 23, and in the next Step 24, gender discrimination is conducted by checking whether or not two or more of the results of the classifications (a), (b) and (c) are the same, with the result of the coincidence check here being output as the gender discrimination result in Step 25.

When the result of the determination in Step 24 is "Male," the discrimination result in Step 25 is YES and control passes to Step 26, in which processing is performed for displaying the message, "Please proceed to the second floor," on the display 5, whereafter execution of the image data processing program 10 is terminated. On the other hand, when the result of the determination in Step 24 is "Female," the discrimination result in Step 25 is NO and control passes to Step 27, in which processing is performed for displaying the message, "Please proceed to the third floor," on the display 5, whereafter execution of the image data processing program 10 is terminated.

Owing to the aforesaid configuration of the gender identification system 1, when a person P about to enter the building presses the pushbutton switch 6, the gender identification system 1 operates as explained above to discriminate whether the person P about to enter is male or female, so that based on the result the person can be directed to the second floor if male and to the third floor if female. A voice announcement may be made in place of or in addition to showing the message on the display 5.

The embodiment shown in FIGS. 9A and 9B is configured to perform gender discrimination based solely on the temperature of the facial region of the person P. However, it is also possible to adopt a configuration that performs gender discrimination using a combination of the person P's facial temperature and palm temperature.

An embodiment will next be explained that partially modifies the embodiment of FIGS. 8, 9A and 9B to distinguish between males and females by combination of the facial temperature and hand temperature of the person P.

Figure 11:
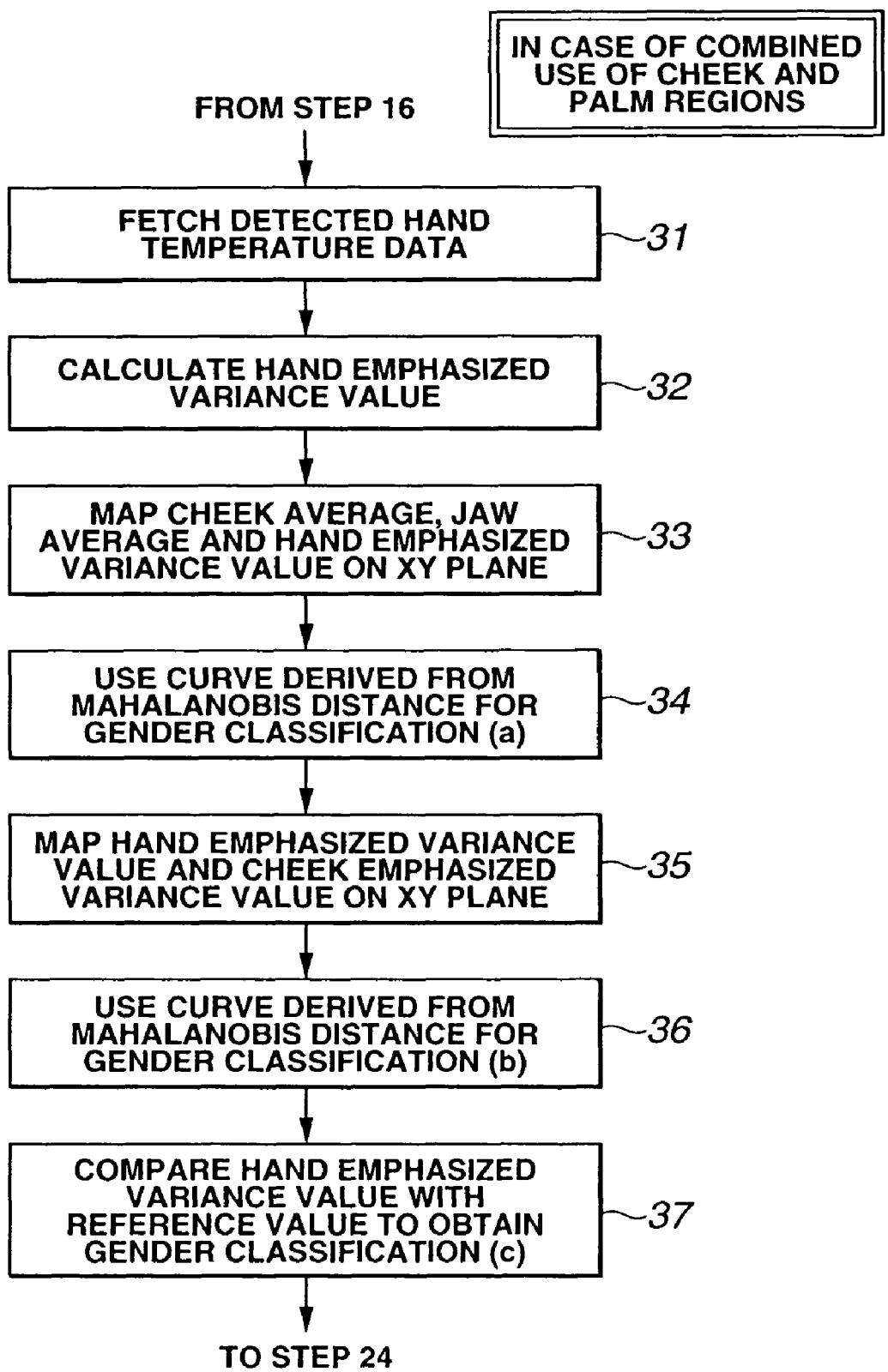
FIG. 11 is a flowchart of the essential portion of an image data processing program using hand temperature and facial temperature in combination.
Figure 12:
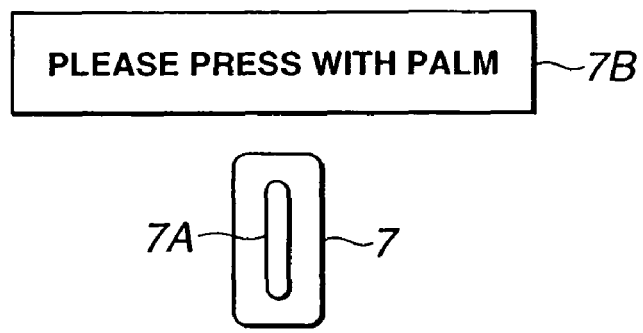
FIG. 12 is diagram showing a hand temperature sampling sensor.

A flowchart of the essential portion of the image data processing program is shown in FIG. 11. In the case of this embodiment, the sensor 7 shown in FIG. 12 is used instead of the pushbutton switch 6 shown in FIG. 8. The sensor 7 is configured by giving the pushbutton switch 6 of FIG. 8 the shape of an automatic door open-close bar as indicated by 7A in FIG. 12 and installing an infrared temperature sensor 7A at this portion so as to detect palm temperature. Here, a plate 7B is installed near the infrared temperature sensor 7A and the instruction, "Please press with palm," is shown on the infrared temperature sensor 7A. This enables detection of the palm temperature.

The data processing included in the routine shown in FIG. 11 for gender discrimination by combined use of palm temperature is basically similar to that shown in FIGS. 9A and 9B but differs therefrom in the point of additionally using a palm emphasized variance value. It is the same as in the preceding embodiment except that the processing of Steps 31-37 shown in FIG. 11 is performed instead of that of Steps 17-22 shown in FIGS. 9A and 9B.

These processing operations will now be explained. After the processing up to Step 16 of FIG. 9A has been completed, the hand emphasized variance value is calculated in Steps 31 and 32, whereafter in Steps 33 and 34, instead of using the cheek emphasized variance value of Step 18, the hand emphasized variance value is used in combination with the cheek average value/jaw average value to obtain classification result (a). Further, in Steps 35 and 36, performed instead of Steps 19 and 20, the hand emphasized variance value and cheek emphasized variance value are used in combination to obtain classification result (b). Next, in Step 37 performed instead of Step 21, the hand emphasized variance value is used to obtain classification result (c). After the three classification results have been obtained in the foregoing steps, the same processing as that in Steps 23 to 27 in FIG. 9B is conducted.

Next, an embodiment of gender discrimination processing in the case of using only the palm temperature will be explained.

In this case, the image data processor 3, monitor unit 4 and display 5 of the configuration shown in FIG. 8 are used and, in addition, the sensor 7 shown in FIG. 12 is used in place of the pushbutton switch 6. And as regards the data processing in this case, the processing shown in FIG. 13 is conducted instead of that of Steps 11-24 shown in FIGS. 9A and 9B.

Figure 13:
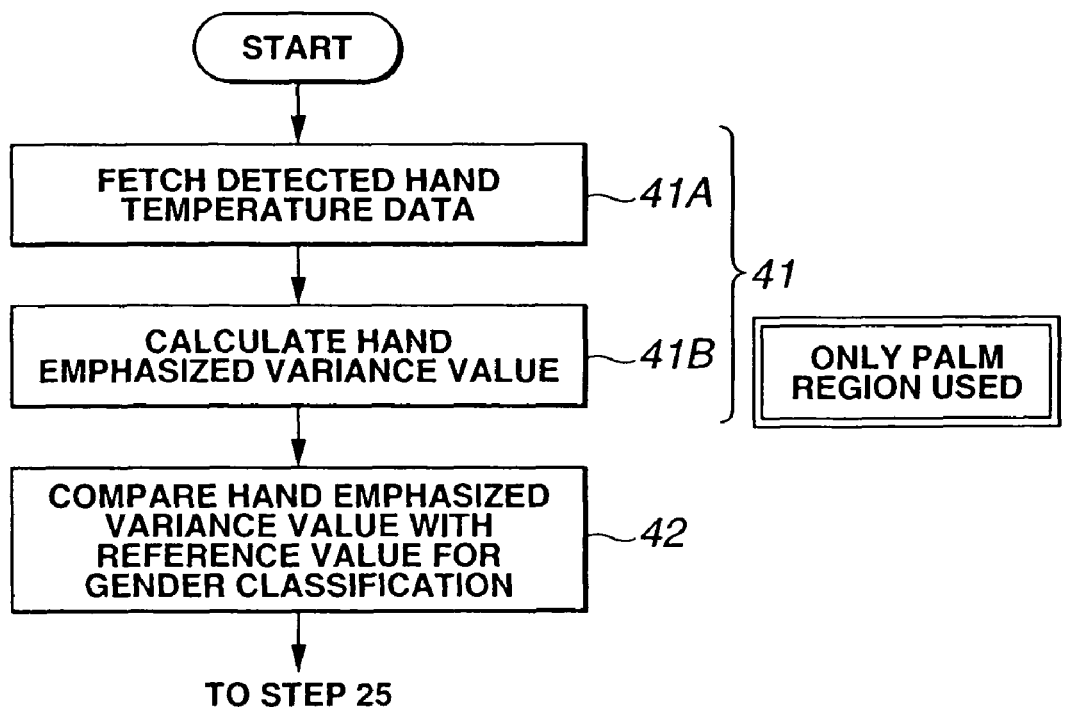
FIG. 13 is a flowchart of the essential portion of an image data processing program using only the temperature of the palm of the hand.

In Steps 41A and 41B constituting Step 41 in FIG. 13, the same processing as that in Steps 31 and 32 in FIG. 11 is conducted to fetch the palm temperature and calculate the emphasized variance value thereof. The palm emphasized variance value calculated in Step 42 is compared with a reference value determined beforehand to perform gender discrimination. The ensuing processing is the same as that of Step 25 onward in FIG. 9B.

Next, an embodiment of gender discrimination processing in the case of using a color image of the moustache region in addition to the cheek temperature and jaw region temperature will be explained. This embodiment takes a visible-light image of a moustache region for use in combination with cheek temperature and jaw region temperature, and is therefore configured to comprise not only the television camera 2A shown in FIG. 8 for taking infrared images but also a television camera 2B for taking visible-light images, and to send the visible-light image signal VDB from the television camera 2B for taking visible-light images to the image data processor 3.

Figure 14:
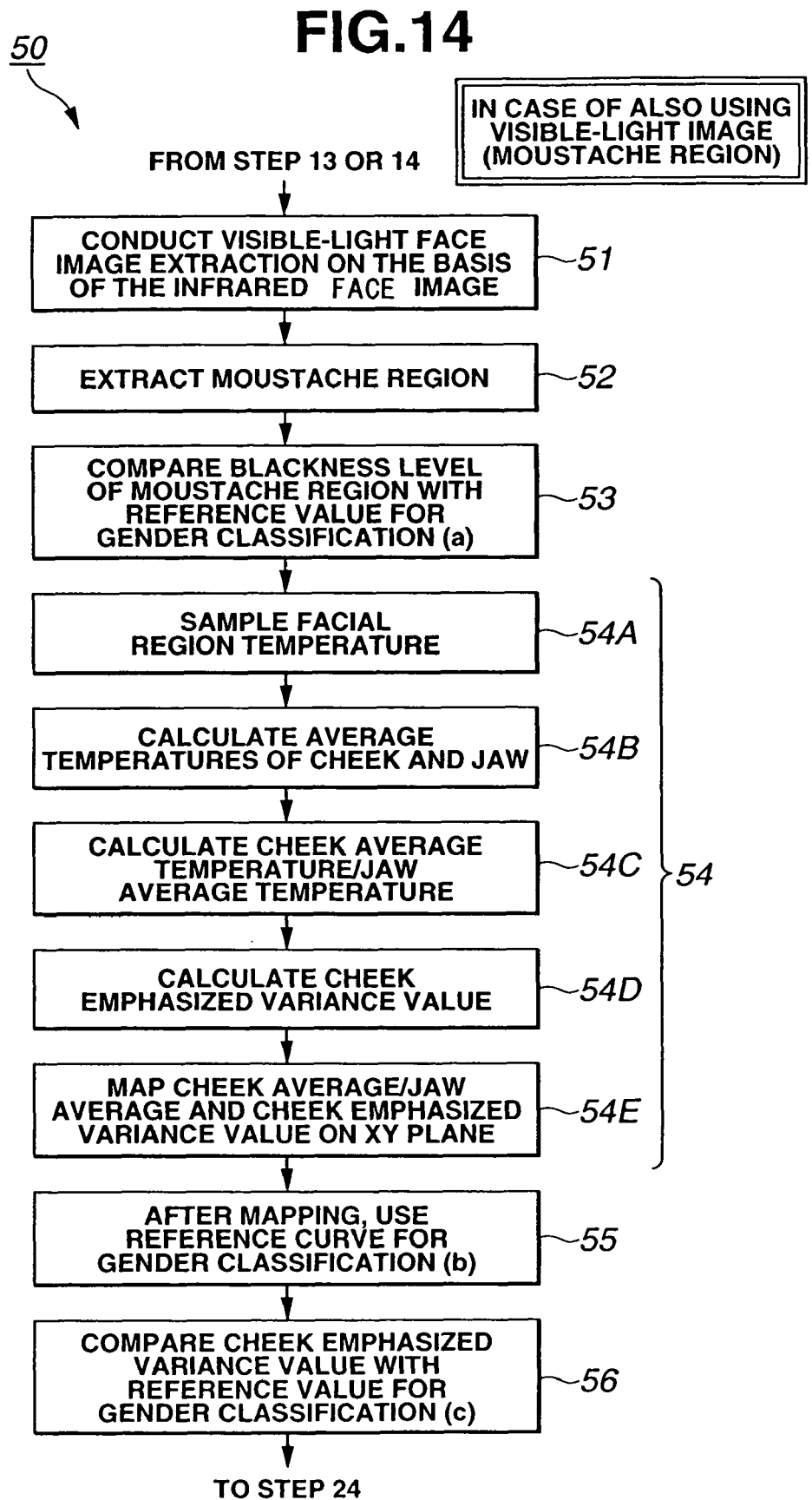
FIG. 14 is a flowchart of the essential portion of an image data processing program using moustache blackness level and facial temperature in combination.

And as regards the data processing in this case, the processing shown in Steps 51-56 of FIG. 14 is conducted instead of that of Steps 15-23 shown in FIGS. 9A and 9B.

In other words, once presence or absence of eyeglasses has been discriminated after extraction of the infrared face image in Steps 11 and 12 of FIG. 9A, visible-light face image extraction is conducted on the basis of the infrared face image Next, in Step 52, a color image of the moustache region of the facial region is extracted from the visible-light image signal VDB of the television camera 2B for taking visible-light images. In Step 53, the color image of the extracted moustache region is compared with a blackness level reference for male moustache region determined beforehand to obtain result (a) classifying the person P as a male if it is equal to or greater than the reference and as female if it is less than the reference. In Steps 54A-54E constituting Step 54, the same processing as that in Steps 15 to 19 in FIG. 19A is conducted. The second classification (b) is performed in Step 55 and the third classification (c) is performed in Step 56. The processing in the ensuing steps is the same that in Step 24 onward in FIG. 9A.

Implementation is also possible according to this same thinking by instead of using the blackness of the mustache region using the color of lipstick, of eye shadow, eyeliner or mascara around the eye, or of the eyebrow itself or the mascara around it, or of cheek rouge, facial skin or the like in a face visible-light image.

Although gender identification system 1 in the foregoing embodiment is configured to discriminate between males and females and operate as an unmanned guide system that gives different guidance in accordance with the discrimination result, the present invention is not limited to this embodiment. For example, by changing the messages displayed in Steps 26 and 27 to "Admittance denied" and "Welcome in," it is possible to permit entry of only women. Further, by replacing the display 5 with a buzzer that sounds only when the determination result is "male," and, for example, applying it to operate in response to the opening of a door at the entrance to a ladies' dressing room or restroom, operation as a security system for preventing entry of males can be realized.

Although this embodiment is configured to perform gender discrimination based on the person P's facial temperature, palm temperature or the like, it is possible to enhance the accuracy of gender discrimination by additionally incorporating in combination a gender discrimination method using the color of eye shadow, eyeliner or mascara around the eye, of the eyebrow itself or mascara around it, of cheek rouge applied to the cheek, of lipstick applied to the lips or of facial skin, or the color of skin blackened by beard from cheek to jaw or moustache or of the beard/moustache itself, or the like.

Other applications that can be mention include the following.

A configuration that can automatically collect gender-specific statistics regarding persons entering department stores, various kinds of shopping centers, shops and amusement facilities, thereby enabling sales system and facility improvement based on the statistical results.

The gender identification of the present invention can be used in combination with a personal identity verification system to achieve a more robust security system.

The present invention provides the effects set out below.

Gender discrimination using a bio-characteristic can be achieved uninfluenced by factors a person can modify at will, such as clothing, hairstyle, makeup, gait and other aspects of appearance, and the voice. When only a bio-characteristic is used, gender discrimination is possible irrespective of race. Gender discrimination is possible without contacting the subject. Gender discrimination is possible unaffected by ambient temperature. Gender discrimination is possible irrespective of presence of eyeglasses. Highly reliable gender discrimination can be achieved by performing discrimination based on different characteristics in combination. Even a person for whom a bio-characteristic cannot be distinguished can be gender-identified by concomitant use color information on different regions of the face.

INDUSTRIAL APPLICABILITY

As set out in the foregoing, the gender identification method in accordance with the present invention enables gender discrimination using a bio-characteristic uninfluenced by factors a person can modify at will, such as clothing, hairstyle, makeup, gait and other aspects of appearance, and the voice, and is useful for structuring a highly reliable gender identification system.

The invention claimed is:

1. A gender identification method for discriminating whether a human subject of discrimination is male or female, which gender identification method comprises: obtaining infrared face image data on the subject using an image signal from a television camera; using a processing device to perform sampling of the cheek region and jaw region temperatures of the subject based on the infrared face image data; calculating the averages of the temperatures; calculating cheek data/jaw data and a cheek emphasized variance value; mapping the cheek data/jaw data and cheek emphasized variance value on an XY plane; conducting first gender discrimination; conducting second gender discrimination using the cheek data/jaw data and third gender discrimination using the cheek emphasized variance value; and conducting gender identification of the subject in accordance with agreement between two or more of the first to third gender discrimination results.

* * * * *